(12) United States Patent
Robinson et al.

(10) Patent No.: US 6,926,908 B2
(45) Date of Patent: *Aug. 9, 2005

(54) FORMULATION FOR INHALATION

(75) Inventors: Stuart Robinson, Nether Broughton (GB); Susan Stewart Smith, Loughborough (GB)

(73) Assignee: Quadrant Drug Delivery Limited, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/218,448

(22) Filed: Aug. 12, 2002

(65) Prior Publication Data

US 2003/0008013 A1 Jan. 9, 2003

Related U.S. Application Data

(63) Continuation of application No. 09/342,356, filed on Jun. 29, 1999, now Pat. No. 6,451,349.
(60) Provisional application No. 60/097,137, filed on Aug. 19, 1998.

(30) Foreign Application Priority Data

Jun. 30, 1998 (GB) .............................................. 9814172

(51) Int. Cl.[7] ................................................. A61K 9/14
(52) U.S. Cl. .......................... 424/489; 424/45; 424/46; 514/3; 514/5
(58) Field of Search ........................... 424/45, 46, 489; 514/3, 5

(56) References Cited

U.S. PATENT DOCUMENTS

| | | | |
|---|---|---|---|
| 3,515,642 A | 6/1970 | Mima et al. | |
| 5,354,562 A | 10/1994 | Platz et al. | |
| 5,855,913 A | 1/1999 | Hanes et al. | |
| 6,051,256 A | 4/2000 | Platz et al. | |
| 6,451,349 B1 * | 9/2002 | Robinson et al. | ........... 424/489 |

FOREIGN PATENT DOCUMENTS

| | | |
|---|---|---|
| CA | 2136704 | 11/1994 |
| DE | 1 227 855 | 11/1966 |
| EP | 072 046 | 2/1983 |
| EP | 542 314 | 5/1993 |
| WO | 92/18164 | 10/1992 |
| WO | 94/08627 | 4/1994 |
| WO | 95/00127 | 1/1995 |
| WO | 95/23613 | 4/1995 |
| WO | 95/24183 | 9/1995 |
| WO | 96/32149 | 10/1996 |
| WO | 97/35562 | 10/1997 |

OTHER PUBLICATIONS

Forbes et al. (1998) "Water vapour sorption sudies on the physical stability of a series of spray–dried protein/sugar powders for inhalation" *J Pharm Sci* 87:1316–1321.
Veber et al. (1980) Preparations releasing cells from animal tissues or surfaces of cultivation vessels Chemical Abstracts 93 Abstract No. 13123.
Yeo et al. (1993) "Formation of microparticulate protein powders using a supercritical fluid antisolvent" *Biotech and Bioeng* 41:341–346.
Chan et al. (1997) "Spray–dried powders and powder blends of recombinant human deoxyriboncuease (rhDNase) for aerosol delivery" *Pharm Res* 14:431–437.
Chan et al. (1998) "Solid state characterization of spray–dried powders of recombinant human deoxyribonuclease (rhDNase)" *J Pharm Sci* 87:647–654.
Niven et al. (1994) "Pulmonary delivery of powders and solutions containing recombinant human granulocyte colony–stimulating factor (rhG–CSF) to the rabbit" *Pharm Res* 11:1101–1109.
Pikal et al. (1997) "The stability of insulin in crystalline and amorphous solids: Observation of greater stability for the amorphous form" *Pharm Res* 14:1379–1387.
Timko et al. (1984) "Thermal analysis studies of glass dispersion systems" *Drug Dev Ind Pharm* 10:425–451.
International Search Report on International Application No. PCT/GB99/02023.

* cited by examiner

*Primary Examiner*—Shelley A. Dodson
*Assistant Examiner*—Konata M. George
(74) *Attorney, Agent, or Firm*—Morrison & Foerster LLP

(57) ABSTRACT

Microparticles, obtainable by spray-drying a substantially pure solution of a therapeutic agent, consist essentially of the agent having its therapeutic activity when administered to the lung. In a preferred embodiment the agent is insulin.

53 Claims, No Drawings

FORMULATION FOR INHALATION

CROSS REFERENCE TO RELATED APPLICATIONS

This application is a continuation of U.S. patent application Ser. No. 09/342,356, filed Jun. 29, 1999, now U.S. Pat. No. 6,451,349, which claims priority to U.S. Provisional Patent Application No. 60/097,137 filed Aug. 19, 1998, and Great Britain Patent Application No. 9814172.4 filed Jun. 30, 1998, the disclosures of each of which are incorporated herein by reference in their entirety.

FIELD OF THE INVENTION

This invention relates to a formulation of a therapeutic agent such as insulin, that is suitable for administration to the lung, and that has good stability.

BACKGROUND OF THE INVENTION

There is now widespread interest in the formulation of therapeutic agents for inhalation. In particular, many efforts have been made to formulate suitable therapeutic agents as dry powders for delivery via inhalers.

Typically, the formulations are produced by drying the active agent in the presence of certain excipients, such as polysaccharides or citrate, to enhance stability during the drying process or in storage.

Insulin is a typical example of a therapeutic agent that can be administered to the lung, by inhalation. As a commercial product, insulin is generally provided in suspension or a solution of low concentration, as a hexamer complexed with zinc Refrigeration is necessary, in order to maintain the stability of such a formulation. Crystalline Zn insulin is stable at neutral pH. The dry powder also requires refrigeration.

CA-A-2136704 discloses a product obtained by spray-drying a medicinal substance such as insulin (among many others) and a carrier. Example 4 discloses spray-drying a clear solution of human insulin soya bean lecithin and lactose WO-A-9735562 again discloses spray-drying a solution of insulin and a polysaccharide. The aim of this combination is to achieve the preferred size range of spray-dried microparticles, for good lung deposition. In Examples 1 and 3, the insulin solution for spray-drying, prior to combination with polysaccharide, is prepared by dissolving zinc insulin in HCl, and then adding NaOH, to pH 7.2. The solutions for spray-drying respectively contain 25 and 6 mg/ml insulin and at least 5.5/7.2% NaCl, based on the combined weight of insulin plus salt.

WO-A-9524183 is directed primarily to a dry powder that comprises insulin and a carrier material, typically a saccharide, in the form of an amorphous powder of microparticles obtained by spray-drying. In addition the Experimental section compares the properties of such microparticles with and without a saccharide excipient. The insulin solution for spray-drying is prepared by dissolving Zn-insulin in citrate buffer, to pH 6.7 ±0.3, to a solids content of 7.5 mg/ml. The powder is held in a container at 10% RH. The formulation without saccharide has considerably lower bioavailability than those with saccharide. For various reasons, this experiment cannot be reproduced: citrate is a buffer at pH 3.0–6.2, and not at pH 6.7; crystalline insulin will not dissolve in pH 6.2 citrate buffer before or after adjustment to pH 7.4 with NaOH; in any case, no alkali addition is specified.

The presence of citrate in dry powder formulations was believed to be necessary to enhance the stability of the final product (Drug Development and Industrial Pharmacy 1984; 10(3):425–451). However, in many cases, the high citrate concentration dilutes the amount of active agent in The initial feedstock, resulting in low amounts of active for drying.

After the date of this invention, Pikal and Rigsbee, Pharm. Rev. 14(10):1379–87 (1997), reported that freeze-dried amorphous insulin was significantly more stable than crystalline insulin at corresponding water contents from 0 to 15% w/w. The mechanism was unclear, but may have been due to configurational differences between the amorphous and crystalline states, the reactive parts of the protein being in closer proximity in the latter. The formulation reported by Pikal and Rigsbee contains no salt, because such low concentrations of insulin (c. 0.5% w/v) are used that manipulation of the pH is unnecessary WO95/23613 discloses a spray-dried DNase formulation. The spray-dried product is in a crystalline form, due primarily to a high concentration of salt. It is stated that high concentrations of salt increases the dispersibility qualities of the final product. In Example 1, the final product contains 60% salt compared with 30% of the DNase.

In summary, the prior art discloses various results of interest but of uncertain commercial significance. None of the procedures described above gives a pure insulin product that is stable, or uses a sufficiently concentrated solution for spray-drying, to be suitable as a commercial procedure The most effective procedures invariably suggest that co-spray-drying of insulin and, say, a saccharide is necessary for best results.

SUMMARY OF THE INVENTION

The present invention is based on the surprising discovery that it is possible to spray-dry a therapeutic agent at higher (and therefore commercially useful) concentrations than have been used previously, without the concomitant production of an undesirable high concentration of salt or other excipients. Such formulations show no substantial loss of activity after the drying process and have extended stability, by comparison with pre-spray-dried preparations. This discovery is of value for au therapeutic agents, in particular proteins and peptides to be administered via the lung.

According to the present invention, microparticles, obtainable by spray-drying a substantially pure solution of a therapeutic agent, consist essentially only of the agent. In a preferred embodiment, the microparticles consist essentially only of insulin and NaCl salt. Such microparticles may be held in a container at greater than 10% RH, and thus essentially at ambient humidity. The insulin microparticles are obtainable by dissolving Zn-insulin in acid, adding alkali to give an insulin solution, e.g. to a pH above 7, and spray-drying the insulin solution (which also contains a salt formed as a result of The dissolution process, or a buffer).

Preferably, the microparticles are non-crystalline amorphous

DESCRIPTION OF THE INVENTION

As indicated above, microparticles of the invention "consist essentially" of the therapeutic agent. This term is used herein to indicate that they are substantially free of polysaccharide, or buffer salt, e.g. citrate, since none is necessary. In general, there will be no polysaccharide present at all, although an amount of up to, say 10% by weight may be tolerated. The absence of polysaccharide has the advantage that a given unit dosage, e.g. a particle, contains essentially only the intended active component. This is an important consideration, for a drug that may be required in large amounts. Another advantage is the avoidance of delivering unnecessary material to a subject. A further advantage is that consistent dosing of the therapeutic agent is facilitated; this is especially important where there is a narrow therapeutic window.

The absence of buffer salt is desirable as it allows a more concentrated feedstock solution of the active agent to be spray-dried resulting in significant cost savings and providing a more commercial-scale process to be adopted.

The term "substantially pure" is used herein to indicate that the feed stock solution to be spray-dried comprises primarily only therapeutic agent and solvent. Again, as described above, there may be a minor amount of solids other than the active agent, but this has no significant effect on the eventual stability of the product.

Insulin microparticles of the invention may include components that are produced during the successive addition of acid and alkali, in preparation of the feedstock, e.g. a salt. For example, NaCl is formed if the acid and alkali are respectively HCl and NaOH. It has been found that the presence of NaCl apparently has no stabilising effect. Indeed, stability may be greater with reduced amounts of salt, again allowing a more concentrated feedstock to be used.

Typically, the solution for spray-drying may contain less than 4% by weight of salt, by weight of total solids. The salt content is based on theoretical considerations, by titration to pH 7. More particularly, this value is calculated by consideration of the molar quantities of the ions added during dissolution. The solution may contain any desired amount of the therapeutic agent, e.g. more than 20, 30 or 50 mg/ml, often up to 100 or 200 mg/ml.

As indicated above, successive addition of acid and alkali apparently destroys the crystalline form of Zn insulin. Zn may dissociate from the hexameric complex but need not be removed. Accordingly, Zn may be present in the microparticles. If desired, this or any other component, other than the therapeutic agent, may be removed, using any suitable technique known to those of skill in the art. In a preferred embodiment for insulin, the Zn is removed from solution prior to spray-drying. This may be achieved by diafiltering the solution according to methods known in the art. The Zn-free insulin may have greater stability than the Zn-containing product. Moisture may also be present As disclosed in more detail in WO-A-9218164, WO-A-9408627 and other Andaris publications, the conditions of spray-drying can be controlled so that microparticles having a defined size range, e.g. 0 1 to 50 μm, can be obtained. The mass median particle size is preferably 1 to 10 μm, when the product is intended for administration by inhalation.

The microparticles (microcapsules) obtained by spray-drying may be solid or hollow Further, the surface may be smooth or "dimpled"; a dimpled surface may be beneficial for inhalation.

The microparticles have good stability and may be maintained as such, i.e. as a dry powder, in a container. During storage or in formulation, they may be mixed with any suitable pharmaceutical agents, carriers, bulking agents etc, and they may be processed by any technique desired to give a product having the properties intended for the ultimate therapeutic use. In particular, the formulation of particles for formulations that can be delivered to the lung, e.g. using a metered dose or dry powder inhaler, are known to those skilled in the art.

The nature of the container is not critical. For example, it may be a glass jar or plastics box. It merely defines a storage environment within which, unlike the prior art and as evidenced below, there is no need to remove moisture or otherwise to control the conditions.

The therapeutic agent may be any protein or peptide having a desired therapeutic effect. Included within the definition of proteins and peptides are functional derivatives, such as glycoproteins. Typical examples of proteins that may be used include enzymes, hormones and blood plasma products. DNase and tryspin are specific examples Others include growth hormone, calcitonins, interferons, interleukin-1 receptor and low molecular weight heparin.

The therapeutic agent may in particular be any of those described in WO-A-9632149. Insulin that is used in the invention may be of any suitable form It may be, for example, bovine or human insulin. Results that have been obtained, regarding the stability of bovine insulin, apparently apply also to human insulin The following Examples illustrate the invention.

EXAMPLE 1

A solution of bovine or human insulin for spray-drying is typically prepared in the following way. 5 g insulin is dissolved in 70 ml 0.05 m HCl, after which the solution is back-titrated with sufficient IM NaOH to reform a solution from the isoelectric point precipitate. According to the final concentration required, water is added to make to volume. Approximately 4.8 ml 1M NaOH is required, in this Example. The solution is then spray-dried using a Mini spray drier with an outlet temperature of approximately 87° C. and a solution feed rate of approximately 0.75 g/min Reverse Phase High Performance Liquid Chromatography (RP-HPLC) was used to assess the stability of insulin, under the following conditions.

| | |
|---|---|
| Column: | Vydac C-18, 5 μm, 30 nm |
| Mobile Phase: | A- 0.1% TFA in water |
| | B- 0.1% TFA in acetonitrile (95%) and water (5%) |
| | Gradient Elution |
| Flow Rate: | 1.5 mL/min |
| Detection: | UV at 220 nm |
| Injection Volume: | 100 μL |

Under these conditions, bovine insulin has a retention time of approximately 7.4 minutes.

A peak attributable to deamidated insulin is located at the failing edge of the main peak. The extent of deamidation is used to indicate stability and is calculated by expressing The area of the deamidation peak as a percentage of the total peak area. Total degradation is expressed as the area of all degrading peaks as a percentage of the total peak area.

TABLE 1

Percentage Total Degradation and Deamidation of Non-Spray Dried Bovine Crystalline insulin

| | 2° C./Ambient RH | | 30° C./60% RH | |
|---|---|---|---|---|
| Time | % Deamidation | % Degradation | % Deamidation | % Degradation |
| Initial | 3.2 | 3.6 | 3.2 | 3.6 |
| 1 month | 3.5 | 3.9 | 4.2 | 5.3 |
| 3 months | 4.4 | 5.6 | 5.8 | 11.0 |
| 6 months | 3.4 | 4.5 | 6.7 | 13.7 |

TABLE 2

Percentage Total Degradation and Deamidation of Insulin Microparticles

| | 2° C./Ambient RH | | 30° C./60% RH | |
|---|---|---|---|---|
| | % Deamidation | % Degradation | % Deamidation | % Degradation |
| Initial | 2.4 | 3.1 | 2.4 | 3.1 |
| 1 month | 2.8 | 3.9 | 3.1 | 4.6 |
| 3 months | 2.0 | 2.7 | 2.6 | 4.1 |
| 6 months | 1.9 | 3.0 | 2.8 | 5.0 |

The results indicate that the extent of both deamidation and total degradation is increased with time, for all the batches evaluated. Additionally, the data suggest that spray drying appears to confer additional stability to the protein, in that the bovine crystalline insulin control suffers increased degradation in comparison to the microparticle formulations at comparable timepoints after storage at 30° C./60% RH.

To investigate whether this was also seen with human insulin, human insulin microparticles were prepared (by the same general procedure as that described above) and placed on accelerated stability at 40° C./75% RH. All samples were analysed by RP-HPLC at the initial time point, and also after 1 week, 2 weeks and 5 weeks.

TABLE 3

Effect of Storage at 40° C./75% RH on the Deamidation and Total Degradation Levels of Human Insulin Recombinant From *E. Coli*

| Storage Time at 40° C./75% RH | % Deamidation | % Total Degradation |
|---|---|---|
| 0 | 0.59 | 0.75 |
| 1 | 1.57 | 4.27 |
| 2 | 1.62 | 5.15 |
| 5 | 2.37 | 8.40 |

TABLE 4

Effect of Storage at 40° C./75% RH on the Deamidation and Total Degradation Levels of Human Insulin Microparticles

| Storage Time at 40° C./75% RH | % Deamidation | % Total Degradation |
|---|---|---|
| 0 | 0.95 | 1.65 |
| 1 | 1.08 | 2.20 |
| 2 | 1.03 | 3.10 |
| 5 | 1.21 | 3.32 |

Comparing Tables 3 and 4, the microparticle formulation of human insulin is less prone to degradation, showing only 3.32% total degradation for the 5 weeks at 40° C./75% RH compared to 8.40% total degradation for the material stored as received under the same conditions.

Pikal and Rigsbee (1997), supra, although working on a lyophilised form of insulin, might be understood to substantiate the findings reported herein.

EXAMPLE 2

A solution of bovine DNase (molecular mass 31 kD) for spray-drying was prepared by dissolving the source material in water containing 1 mM phenylmethylsulphonyl fluoride (PMSF). The PMSF is present to inhibit proteolytic degradation. The resulting feedstock solution comprised 50 mg/ml DNase.

The solution was then spray-dried using a Mini spray drier with an inlet temperature of 130° C., an outlet temperature of 85° C. and a solution feed rate of approximately 0.8 ml/min. The activity was measured by the rate of increase of spectrophotometric absorbance at 260 nm of DNA (hyperchromicity assay), and HPLC gel permeation chromatography was used to assess the physical stability.

Spray-dried DNase retained approximately 90% of its initial activity and showed no change in physical stability. For spray-dried material stored at 40° C./75/% RH and 25° C./60% RH, and source material stored at 25° C./60% RH, there was comparable activity and physical stability at 4 and 8 weeks.

EXAMPLE 3

A solution of bovine trypsin (molecular mass 23.3 kD) for spray-drying was prepared by dissolving the source material (crystallised) in water The resulting feedstock solution comprised 50 mg/ml trypsin The solution was then spray-dried as described in Example 2. Activity was measured against azocasein substrates and HPLC gel permeation chromatography was used to assess the physical stability.

Spray-dried trypsin retained approximately 100% of its initial activity and showed no change in physical stability. A comparison of spray-dried material stored at 4° C., 25° C./60% RH and 40° C./75% RH, and source material stored at 25° C./60% RH, showed substantially no loss in activity or physical stability at 12 weeks.

EXAMPLE 4

A solution of reduced gluthathione (a peptide of molecular mass 307D) for spray-drying was prepared by dissolving the crystalline source material in water. The resulting feedstock solution comprised 100 mg/ml reduced glutathione.

The solution was spray-dried using a Buchi Mini B-191 spray-drier with an inlet temperature of 100° C., an outlet temperature of 74° C., and a solution feed-rate of approximately 1 ml/min. Spray-drying using either compressed air or nitrogen for atomisation of the fluid stream did not result in a significant increase in the level of oxidised glutathione (initially present at 0.8% w/w, increasing to 0.9% w/w).

What is claimed is:

1. Microparticles, obtainable by spray-drying a substantially pure solution of a therapeutic agent, wherein the microparticles consist essentially only of the therapeutic agent having its therapeutic activity when administered to the lung, and further wherein the therapeutic agent is a protein or peptide.

2. Microparticles according to claim 1, wherein the agent is non-crystalline/amorphous.

3. Microparticles according to claim 1 or 2, consisting essentially of the agent and a salt formed in dissolution of the agent.

4. Microparticles according to claim 3, wherein the salt is formed from an alkali and a mineral acid.

5. Microparticles according to claim 4, wherein the microparticles comprise less than 4% salt by weight of total solids.

6. A closed container containing, at ambient humidity, microparticles according to claim 1 or 2.

7. An inhaler device comprising microparticles according to claim 1 or 2.

8. A process for the preparation of microparticles according to claim 1, which comprise spray-drying a substantially pure solution of a therapeutic agent.

9. A process according to claim 8, wherein the solution contains more than 10 mg/ml of agent.

10. A process according to claim 9, wherein the solution contains 20 to 200 mg/ml agent.

11. A process according to claim 9, wherein the solution contains 50 to 100 mg/ml agent.

12. A process according to any of claims 8 to 11, wherein the solution contains less than 4% salt.

13. A process according to any of claims 8 to 11, wherein the solution is free of buffer salt.

14. A process according to claim 12, wherein the solution is free of buffer salt.

15. A process for the preparation of microparticles according to claim 2, which comprise spray-drying a substantially pure solution of a therapeutic agent.

16. A process according to claim 15, wherein the solution contains more than 10 mg/ml of agent.

17. A process according to claim 16, wherein the solution contains 20 to 200 mg/ml agent.

18. A process according to claim 16, wherein the solution contains 50 to 100 mg/ml agent.

19. A process according to any of claims 15 to 18, wherein the solution contains less than 4% salt.

20. A process according to any of claims 15 to 18, wherein the solution is free of buffer salt.

21. A process according to claim 19, wherein the solution is free of buffer salt.

22. Microparticles according to claim 2, wherein the therapeutic agent is a protein or peptide.

23. An inhaler device comprising microparticles according to claim 22.

24. An inhaler device comprising microparticles according claim 3.

25. An inhaler device comprising microparticles according claim 4.

26. An inhaler device comprising microparticles according to claim 5.

27. Microparticles according to claim 22 consisting essentially of the agent and a salt formed in dissolution of the agent.

28. Microparticles according to claim 27, wherein the salt is formed from an alkali and a mineral acid.

29. Microparticles according to claim 28, wherein the microparticles comprise less than 4% salt by weight of total solids.

30. A process for the preparation of microparticles according to claim 22, which comprise spray-drying a substantially pure solution of a therapeutic agent.

31. A process according to claim 30, wherein the solution contains more than 10 mg/ml of agent.

32. A process according to claim 31, wherein the solution contains 20 to 200 mg/ml agent.

33. A process according to claim 31, wherein the solution contains 50 to 100 mg/ml agent.

34. A process according to any of claims 30 to 33, wherein the solution contains less than 4% salt.

35. A process according to any of claims 30 to 33, wherein the solution is free of buffer salt.

36. A process according to claim 34, wherein the solution is free of buffer salt.

37. A process for the preparation of microparticles according to claim 3, which comprise spray-drying a substantially pure solution of a therapeutic agent.

38. A process according to claim 37, wherein the solution contains more than 10 mg/ml of agent.

39. A process according to claim 38, wherein the solution contains 20 to 200 mg/ml agent.

40. A process according to claim 38, wherein the solution contains 50 to 100 mg/ml agent.

41. A process according to claim 37, wherein the solution contains less than 4% salt.

42. A process according to claim 37, wherein the solution is free of buffer salt.

43. A process according to claim 38, wherein the solution contains less than 4% salt.

44. A process according to claim 38, wherein the solution is free of buffer salt.

45. A process according to claim 39, wherein the solution contains less than 4% salt.

46. A process according to claim 39, wherein the solution is free of buffer salt.

47. A process according to claim 40, wherein the solution contains less than 4% salt.

48. A process according to claim 40, wherein the solution is free of buffer salt.

49. A closed container containing, at ambient humidity, microparticles according to claim 3.

50. A closed container containing, at ambient humidity, microparticles according to claim 4.

51. A closed container containing, at ambient humidity, microparticles according to claim 5.

52. A closed container containing, at ambient humidity, microparticles according to claim 15.

53. A composition comprising microparticles according to claim 1, admixed with a carrier or bulking agent.

* * * * *